(12) United States Patent
Collingwood et al.

(10) Patent No.: US 6,933,718 B2
(45) Date of Patent: Aug. 23, 2005

(54) QUANTIFICATION METHOD AND SYSTEM FOR CORROSION AND DAMAGE ASSESSMENT

(75) Inventors: Michael R. Collingwood, Huntington Beach, CA (US); Steven G. Keener, Trabuco Canyon, CA (US)

(73) Assignee: The Boeing Company, Seattle, WA (US)

( * ) Notice: Subject to any disclaimer, the term of this patent is extended or adjusted under 35 U.S.C. 154(b) by 302 days.

(21) Appl. No.: 10/166,561

(22) Filed: Jun. 10, 2002

(65) Prior Publication Data

US 2003/0025497 A1 Feb. 6, 2003

Related U.S. Application Data

(60) Provisional application No. 60/297,535, filed on Jun. 12, 2001.

(51) Int. Cl.[7] .......................... G01N 27/90; G01N 27/82
(52) U.S. Cl. ....................... 324/242; 324/225; 324/238; 324/240; 702/38; 702/105
(58) Field of Search ................................ 324/220, 230, 324/232, 238, 240, 242; 702/38, 105, 193, 198

(56) References Cited

U.S. PATENT DOCUMENTS

| | | |
|---|---|---|
| 2,572,908 A | 10/1951 | Brenholdt |
| 3,340,466 A | 9/1967 | Ono |
| 3,450,986 A | 6/1969 | Chapman et al. |
| 3,764,897 A | 10/1973 | Greenwood |
| 3,968,681 A | 7/1976 | Cornforth et al. |
| 4,146,837 A * | 3/1979 | Bashkirov .................... 324/225 |
| 4,271,393 A | 6/1981 | Hansen et al. |
| 4,292,588 A | 9/1981 | Smith |
| 4,503,392 A | 3/1985 | Fastritsky et al. |
| 4,652,822 A * | 3/1987 | Wallace ....................... 324/232 |
| 4,652,823 A | 3/1987 | Sutton |
| 4,727,322 A | 2/1988 | Lonchampt et al. |
| 4,755,753 A | 7/1988 | Chern |
| 4,757,259 A | 7/1988 | Charpentier |
| 4,843,319 A | 6/1989 | Lara |
| 4,843,320 A | 6/1989 | Spies |
| 4,954,778 A | 9/1990 | Champonnois et al. |
| 5,028,100 A | 7/1991 | Valleau et al. |
| 5,059,903 A | 10/1991 | Otaka et al. |
| 5,180,969 A | 1/1993 | Kwun et al. |
| 5,182,513 A * | 1/1993 | Young et al. ................ 324/232 |
| 5,237,271 A | 8/1993 | Hedengren |
| 5,311,128 A | 5/1994 | Lareau et al. |
| 5,371,462 A | 12/1994 | Hedengren et al. |
| 5,485,082 A | 1/1996 | Wisspeintner et al. |
| 5,491,409 A | 2/1996 | Flora et al. |
| 5,510,709 A | 4/1996 | Hurley et al. |
| 5,602,474 A | 2/1997 | Morrey, Jr. |
| 5,610,517 A | 3/1997 | Ma et al. |
| 5,648,721 A * | 7/1997 | Wincheski et al. ......... 324/240 |
| 6,037,768 A | 3/2000 | Moulder et al. |
| 6,285,183 B1 | 9/2001 | Collingwood et al. |
| 6,504,363 B1 * | 1/2003 | Dogaru et al. .............. 324/235 |
| 6,545,469 B1 * | 4/2003 | Batzinger et al. ........... 324/238 |

FOREIGN PATENT DOCUMENTS

| | | | |
|---|---|---|---|
| EP | 0 332 048 A2 | 9/1989 | |
| GB | 2 090 2977 A | 7/1982 | |
| SU | 789730 B * | 12/1980 | ......... G01N/27/90 |
| SU | 832442 B * | 5/1981 | ......... G01N/27/86 |

* cited by examiner

Primary Examiner—Jay Patidar
Assistant Examiner—Darrell Kinder
(74) Attorney, Agent, or Firm—Alston & Bird LLP

(57) ABSTRACT

The present invention provides a method for the direct measurement and quantification of the material volume loss on and beneath a first surface of a substrate and thus provides an accurate depiction of the profile of the substrate. The method of the invention comprises inducing multiple eddy currents in a test substrate to determine volume loss.

22 Claims, 6 Drawing Sheets

QUANTIFICATION METHOD AND SYSTEM FOR CORROSION AND DAMAGE ASSESSMENT

CROSS REFERENCE TO RELATED APPLICATIONS

This application claims the benefit of U.S. Provisional Patent Application No. 60/297,535, filed Jun. 12, 2001.

FIELD OF THE INVENTION

This invention relates to a method for determining defects or flaws on metal components due to corrosion or other damage. More specifically, this invention relates to a method for evaluating corrosion on and beneath the inspection surface using duel frequency eddy current signals.

BACKGROUND OF THE INVENTION

Corrosion damage is a significant threat to the safe operation of both military and commercial aircraft. Failure to detect and correctly quantify corrosion damage can lead to failure of various aircraft components. Corrosion damage is an even more significant problem with military aircraft due to the extreme environments in which they must operate.

Systems for determining damage to metal structures are known. One such system includes a thermographic system for detecting exfoliation corrosion on aircraft skins. However, this technique is limited to flat surfaces and only presents images that are visually compared with surrounding areas.

Traditional impedance plane eddy current techniques are also used to evaluate corrosion damage and material volume loss on aircraft skins. The eddy current response from a test sample is compared to the eddy current response from a reference standard. The result is a subjective evaluation of whether or not the test sample is better or worse than the reference standard. The technique is limited by the inability to produce corrosion reference standards with quantifiable defects. As a result, assessment of corrosion damage in an aircraft metallic structure has required a complete understanding of the physics involved and extensive experience of a specialist in complex and time consuming inspection techniques currently available in the industry. In other words, corrosion damage determination has been highly subjective and quality depends to a large degree upon the individual conducting the evaluation.

Eddy current inspection methods are known for detecting cracks and flaws in aircraft skin metal immediately surrounding rivets without requiring the removal of rivets or manual scanning. Such methods include positioning a probe concentrically around the rivet. In such methods, the inspection probe either provides a zero reading corresponding to no cracks or defects, or a non-zero reading corresponding to one or more cracks or defects in the surface. Thus, known systems locate only two-dimensional anomalies, such as cracks in the surface around the rivet. See U.S. Pat. No. 5,510,709.

Other known systems detect surface corrosion on metallic structures that are insulated by a coating or cover, or covered with marine growth. Such systems provide alternating magnetic fields to induce an eddy current. See U.S. Pat. No. 5,491,409.

Further, commonly assigned U.S. Pat. No. 6,285,183 discloses methods and apparatuses for determining corrosion and material volume loss at and beneath the surface to a depth of up to about 0.100 inch using eddy current principles, the entire contents of which are incorporated by reference and made a part of this application herein.

The great majority of damage to structural members due to corrosion originates from corrosion damage within the fastener holes and beneath the surface at faying surfaces. While some of the above-identified methods and devices are applicable to evaluating corrosive damage just beneath the surface at faying surfaces, a more precise system for determining deeper sub-surface corrosion and/or material volume loss is desirable.

SUMMARY OF THE INVENTION

According to one embodiment, the present invention provides a method for the direct measurement and quantification of the volume loss along the surface and sub-surface of a substrate and thus more accurately depicts the surface and sub-surface profile of a substrate than conventional processes which can only provide comparative measurements of a surface profile or two dimensional anomalies on a test surface. In addition, the method of the invention can be used with various types of materials and can be used to measure volume losses even on non-planar surfaces such as around fasteners or inside fastener holes where corrosion defects often originate. The method of the invention allows a contour or three-dimensional map of the surface of substrate to be produced illustrating the material lost due to corrosion or damage. Even more advantageously, the method of the invention allows for the early determination of metal loss due to corrosion and damage thereby allowing replacement or repair of the test substrate prior to failure of the substrate.

In a further embodiment, one method of the invention comprises inducing a plurality of eddy currents in a test substrate, measuring the magnitude of the eddy current within the substrate at a plurality of locations on the surface and sub-surface of the test substrate, and converting the measured eddy current magnitudes at the locations to corresponding volume losses on the surface and sub-surface of the substrate using the eddy current magnitude measurements of a reference substrate having defects of predetermined volume loss. The measurements of the eddy current magnitude on the test substrate are converted by multiplying a normalized eddy current magnitude for a sector on the surface of the test substrate both by a predetermined calibration factor ($C_f$) representing volume per unit area eddy current magnitude, and the surface area of the sector to provide volumetric measurements of the metal loss in the sector. The calibration factor ($C_f$) is determined by measuring the magnitude of the eddy current produced for a plurality of defects having predetermined volume losses on the surface of a reference substrate.

In a specific method embodiment of the invention, the volume loss on the surface and sub-surface of a metal test substrate is measured by first calibrating the system using a reference substrate and then using the system to test the surface of a substrate. The system calibration comprises inducing an eddy current in a reference substrate having a an area comprising a plurality of sectors of predetermined surface area and predetermined volume loss such that at least a portion of the sectors have no volume loss, or minimum volume loss, and at least a portion of the sectors have a positive volume loss. The magnitude of the eddy current produced in the reference substrate is measured on the surface of the substrate at a plurality of locations within each sector and the eddy current magnitudes measured for the locations in the sectors having no volume loss, or minimum volume loss, are averaged to provide a threshold level (T). The threshold level (T) is then subtracted from the measured magnitudes for the locations in the sectors having positive volume loss to provide a normalized eddy current magnitude for each location. Preferably, the normalized eddy current magnitudes measured at each of the locations in the sector having the greatest volume loss are summed to provide a normalized eddy current magnitude for the sector of greatest volume loss. The predetermined volume of the sector of greatest volume loss is then divided by both the normalized eddy current magnitude for the sector of greatest volume loss and the surface area of the sector of greatest volume loss to produce a calibration factor ($C_f$) representing the measured volume per unit area eddy current magnitude.

Once the process is calibrated, a surface is tested by inducing eddy currents in the test substrate and measuring the magnitude of the eddy current produced within the substrate on the surface of the substrate at a plurality of locations within sectors of predetermined surface area. As in the calibration process, the locations of no volume loss, or minimum volume loss, are averaged to produce a threshold value ($T_{test}$). The measured eddy current magnitudes at the locations are decreased by the threshold value ($T_{test}$) to produce normalized eddy current magnitudes at the locations. The normalized eddy current magnitudes for the locations within each sector are summed to produce a normalized eddy current magnitude for each sector. Accordingly, the normalized eddy current magnitudes for each sector are multiplied by the calibration factor ($C_f$) and by the surface area of the sector to provide quantitative measurements of the volume loss for the sectors thereby providing a surface profile of volume loss on the test surface.

The present invention also includes a system for producing a surface profile of the volume loss along the surface and sub-surface of a metal substrate comprising eddy current inducers for inducing a plurality of eddy currents in a test substrate, a measurement device for measuring the magnitude of the eddy current within the substrate at a plurality of locations on the surface of the substrate, and a converter for converting the measured magnitudes at the locations to corresponding volume losses on the test surface. Preferably, the inducers and measurement device comprise an eddy current inspection probe having an inspection surface that corresponds to the test surface.

These and other features and advantages of the present invention will become more readily apparent to those skilled in the art upon consideration of the following detailed description that describes both the preferred and alternative embodiments of the present invention.

BRIEF DESCRIPTION OF THE INVENTION

DETAILED DESCRIPTION OF THE INVENTION

The present invention will be described more fully hereinafter with reference to the accompanying drawings, in which preferred embodiments of the invention are shown. This invention can, however, be embodied in many different forms and should not be construed as limited to the embodiments set forth herein; rather, these embodiments are provided so that this disclosure will be thorough and complete, and will fully convey the scope of the invention to those skilled in the art.

Figure 1:
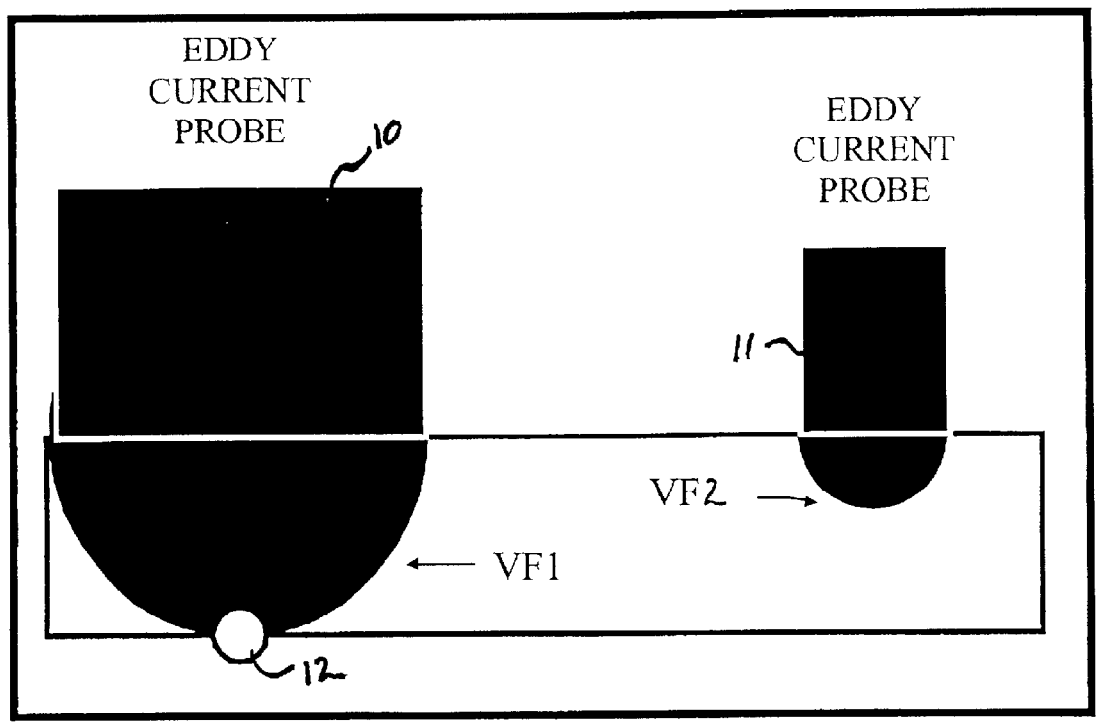
FIG. 1 shows the proportion of two eddy current field volumes, (VF1, VF2) relative to flaw volume.

The present invention overcomes the problems associated with detecting and evaluating corrosion that is deeper than 0.100 inch from the inspection surface. The limitations associated with conventional eddy current inspection systems are obviated by the methods and apparatuses of the present invention. Known eddy current corrosion detection systems are unable to detect sub-surface corrosion because the eddy current field being used cannot penetrate into the material being inspected. Deeper penetration of the eddy current field has been attempted by lowering the operating frequency, but this has led to a decrease in system sensitivity. The sensitivity is lost because the volume of the eddy current field becomes much larger than the volume of the target corrosion being detected. The higher the proportion of eddy current field volume to flaw volume, the lower the obtainable resultant sensitivity. As shown in FIG. 1, eddy current probes 10, 11 operating frequencies F1 and F2, respectively, create eddy current fields, VF1 and VF2, to detect defect or flaw 12. In an alternate embodiment, not shown, it is understood that one probe can be substituted for the multiple probes to achieve the same result.

The current invention overcomes this problem. The method detailed below can accurately measure corrosion damage at depths ranging from 0.100 inch to over 0.250 inch including corrosion on the surface opposing the inspection surface. The method can potentially measure corrosion on surfaces up to 0.750 inch from the inspection surface.

Metal and other substrates can be inspected to a great degree of accuracy and to as yet unknown detection levels according to the methods described herein. The methods and apparatuses of the present invention can accurately measure corrosion damage at depths ranging from about 0.100 inch to about 0.250 inch, or more. Corrosion on the surface opposing the inspection surface can be measured accurately at a distance up to 0.750 inch from the inspection surface.

The current invention overcomes the depth limitations of the previous invention through a process known as frequency mixing or frequency slicing, whereby a plurality of eddy current fields are induced in tandem, such that they occur in the substrate material substantially simultaneously during data acquisition. U.S. Pat. No. 6,285,183 disclosed the use of a single frequency eddy current signal operating in the 180.0 kHz. to 200.0 kHz. range. This frequency range is typically accepted as the one providing the greatest depth of penetration in common aluminum while maintaining an acceptable sensitivity level.

Figure 2:
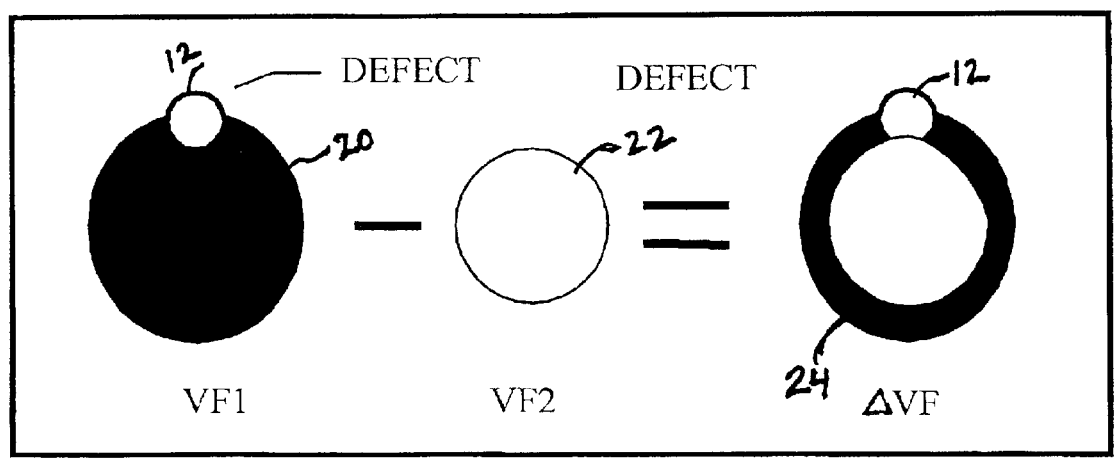
FIG. 2 shows the difference, $\Delta$VF, in eddy current fields, VF1–VF2.

The method and apparatuses of the present invention uses multiple frequency eddy current signals operating together, both at lower frequencies than previously accepted. Two frequencies, F1 and F2, work in combination to achieve greater depth of penetration while sustaining an acceptable sensitivity level. Corrosion that occurs deep in the sample, or on the far or opposing surface, can be interrogated by an eddy current field operating at a very low frequency F1. This is especially advantageous since the opposing surfaces, after assembly, are most often inaccessible to visual or physical inspection. As shown in FIG. 2, the eddy current field, VF1, created by probe 10 with frequency F1 is minutely affected by the presence of the corrosion but the effect is negligible given the relatively large resulting volume, VF1, 20 of the eddy current field. A second eddy current field is created by a second eddy current probe 11 operating at a frequency F2. Both the F1 and F2 frequencies operate in the probe coils either simultaneously or by multiplexing. Preferably, the F2 frequency is higher than the F1 frequency and therefore does not penetrate as deeply into the sample. As a result, the eddy current field created by eddy current probe 11 operating at frequency F2 produces a relatively smaller volume, VF2, 22.

The method of the present invention works by calculating the difference between the VF2 eddy current field 22 and the VF1 eddy current field 20. The difference is an eddy current field volume that equates to the very outer shell of the F1 eddy current field. This remaining volume, $\Delta VF$, 24 is very small compared to the original VF1, 20 and is significantly more sensitive to corrosion occurring at the deeper regions of the sample reached by the VF1 eddy current field.

Figure 3:
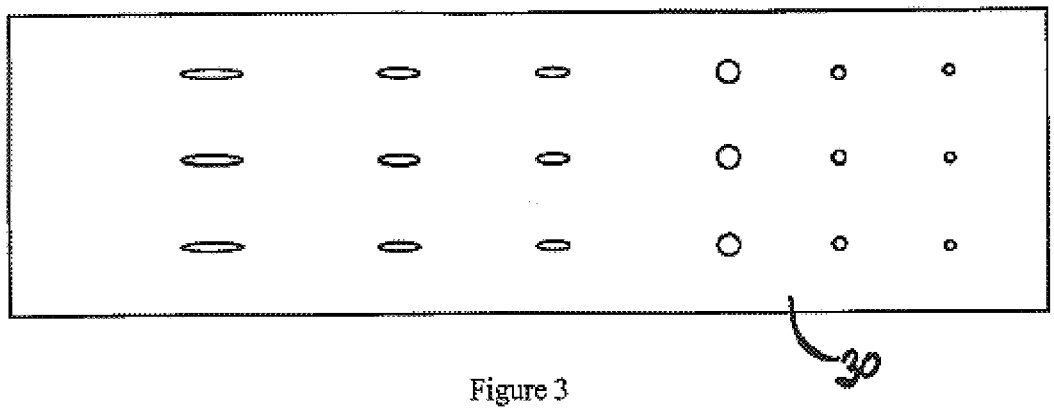
FIG. 3 shows a reference standard used in calibration.
Figure 4:
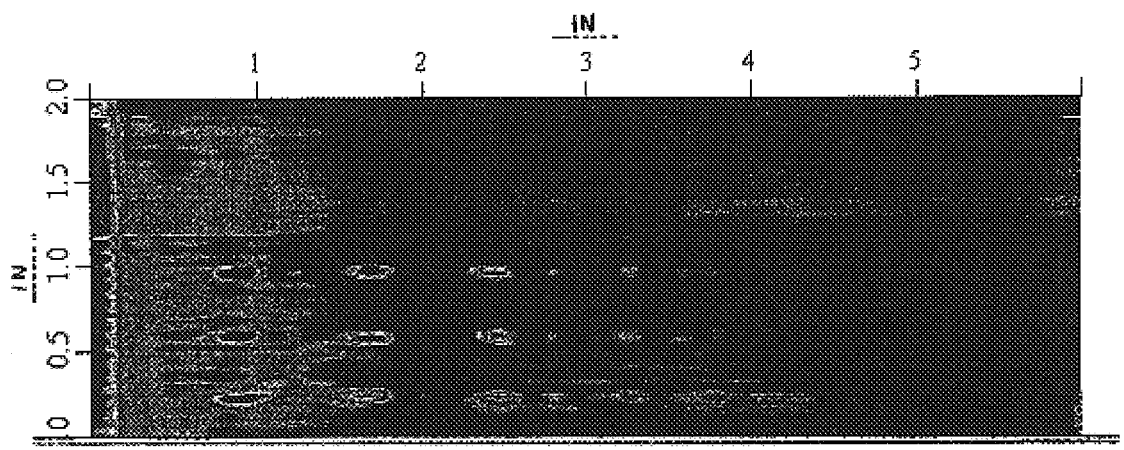
FIG. 4 shows a resulting corrosion map.

Once the data with enhanced accuracy is acquired, it is then subjected to the same analysis that is disclosed in U.S. Pat. No. 6,285,183. The volume of the material loss is then calculated. To acquire the enhanced accurate data, the following detailed steps are required. First, any multi-frequency eddy current instrument capable of running two or more frequency signals through a single eddy current coil are used, as would be readily understood by one skilled in the field of volumetric measurement. The eddy current field, VF1, created by the initial frequency F1 is determined by calculation or by reference to standard depth of penetration reference tables. The desired frequency is the unique frequency that will establish a depth of penetration equal to the material thickness, or lower limit of depth at which the corrosion is to be measured. The second current field, VF2, created by the second frequency F2 is determined by either selecting a higher multiple of F1 (e.g. F1=2 KHz and F2=8 KHz) or by calculating the frequency required to achieve a depth of penetration equal to the upper limit of the corrosion to be measured. The choice of F2 may be limited by the capabilities of the instrument used. As set forth in parentheses above, the instrument selected had a multiple of four (4) resulting in the varying frequencies. The instrument is calibrated first using F1 by setting the gain and phase rotation that provides the optimum signal for the back surface or the deeper depth. The instrument is then calibrated for F2 by adjusting the gain and phase rotation to optimize the signal from the shallow depth. The outputs of the two frequencies F1, F2 are then mixed to produce the greatest difference between them in response to reference corrosion at the desired depth. The final step of the calibration is to scan the eddy current coil over a reference standard 30, of the type shown in FIG. 3, having simulated levels of corrosion on the side remote from the eddy current coil. The result is a corrosion map such as that shown on FIG. 4.

Figure 5:
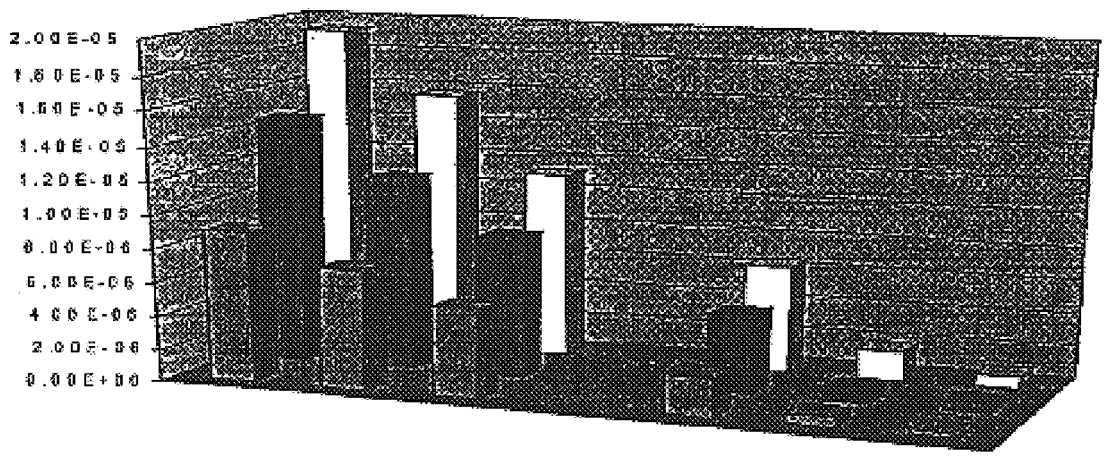
FIG. 5 shows the calculated volumes of the simulated corrosion defects.
Figure 6:
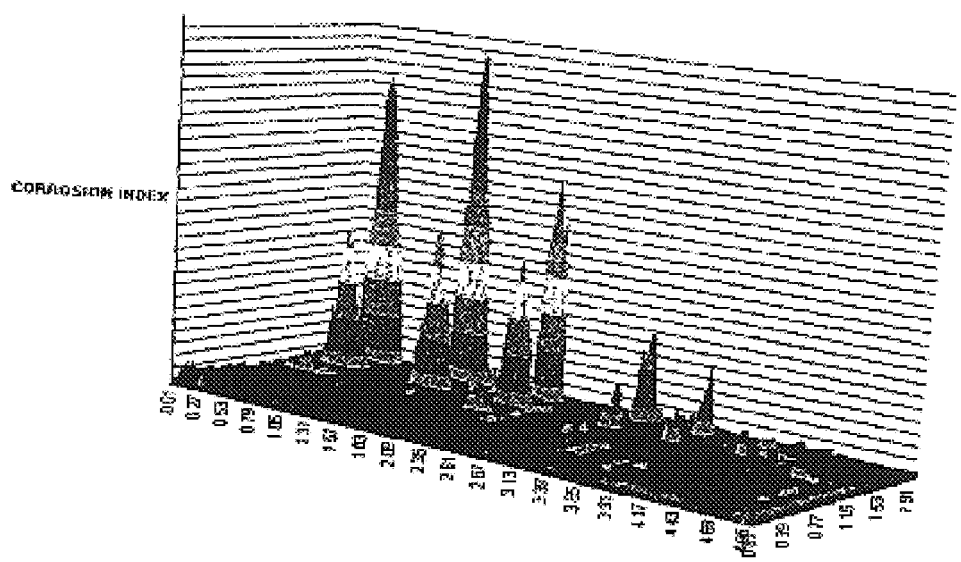
FIG. 6 shows a resulting map showing the volume of material lost due to corrosion.
Figure 7:
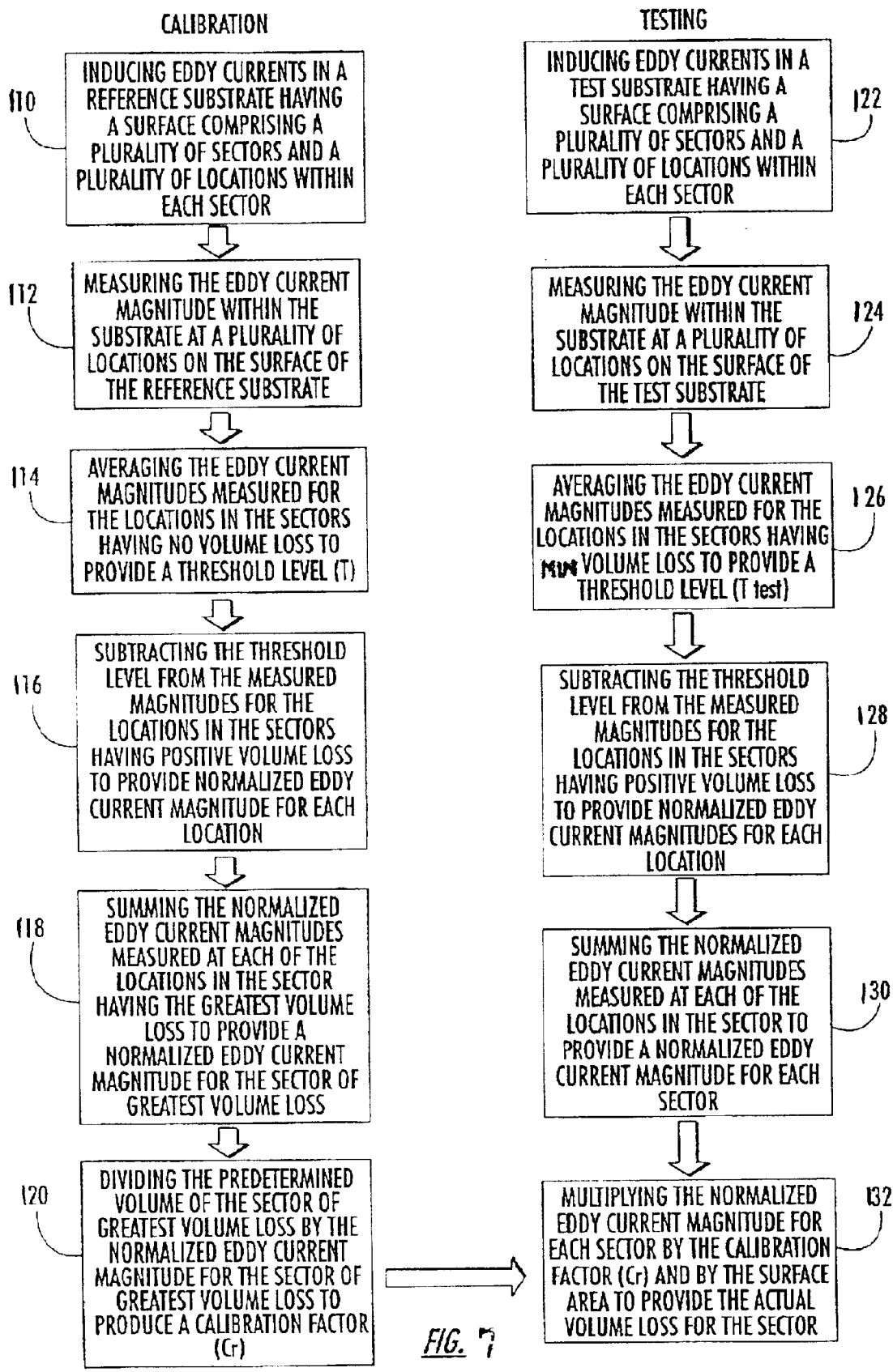
FIG. 7 is a flow chart illustrating calibration and test sequences of the invention.
Figure 9:
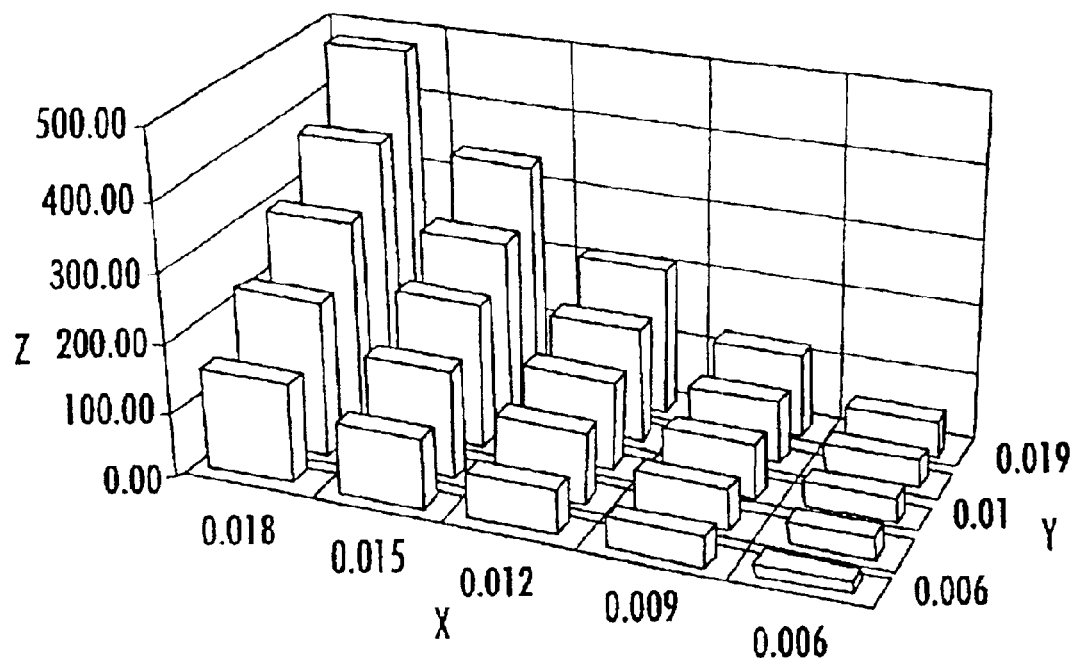
FIG. 9 is a three dimensional graph showing the calculated volumes of defects which simulate corrosion pitting in a reference standard.

The calibration method used in conjunction with the present invention is delineated in the flow chart and is illustrated in FIG. 7. In the method of the invention, a reference substrate having surface defects or flaws of known volume is first selected having the same chemical composition and mechanical properties, such as temper or hardness of the component or test article substrate to be tested. For example, as shown in FIG. 9, the volumes for a series of surface defects are calculated for a reference substrate. The surface defects of the reference substrate are selected to resemble corrosion pitting and consist of a series of holes of varying depth in inches as illustrated along the X axis of FIG. 9 and of varying diameter as measured in inches along the Y axis of FIG. 9. The reference substrate is preferably divided into sectors of predetermined surface area with each sector containing no more than one defect. In FIG. 5, the calculated volumes based upon the dimensional characteristics for the defects in each sector appear along the Z axis and are plotted in cubic inches$\times 10^{-6}$. FIG. 6 is the actual C-Scan of the calculated volumes of FIG. 5 contained in the reference standard calibration plate 30. See FIG. 3. The eddy current C-Scan (FIG. 6) demonstrates there is good agreement with the calculated volumes of FIG. 5. In FIG. 6, the relative magnitudes of the corrosion defects or flaws are shown, in the Z axis demonstrating the validity of the C-Scan to the calculated values of the reference standard. Additionally, the reference substrate typically has sectors of no volume loss to aid in the calibration of the system as described herein.

The methods of the present invention accurately measure corrosion damage occurring at a depth exceeding about 0.100 inch, preferably from about 0.100 inch to about 0.250 inch, and under certain conditions depths in excess of 0.250 inch. In addition, corrosion can accurately be measured on the surface opposing the inspection surface, preferably up to a depth of about 0.750 inch.

Figure 8:
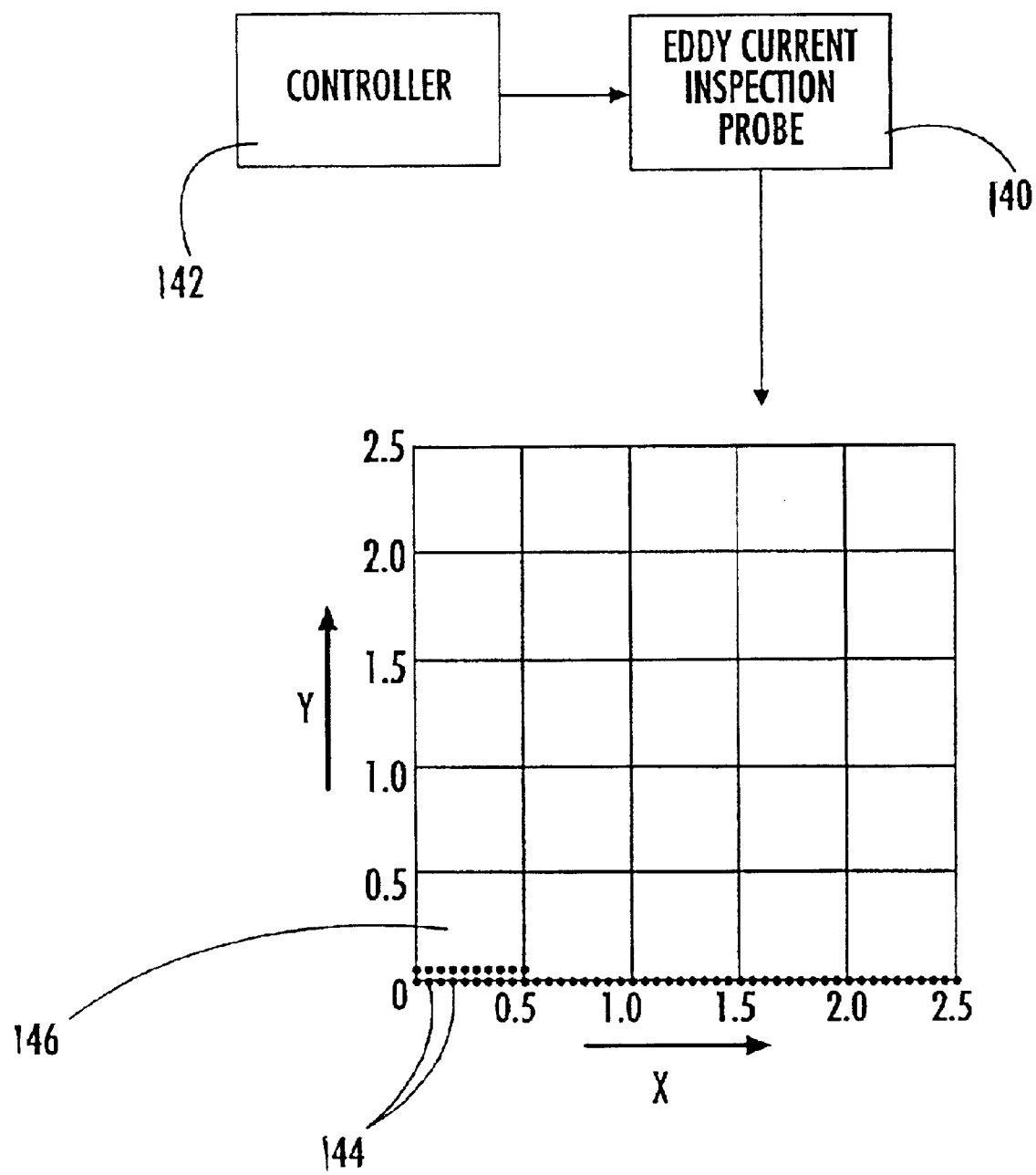
FIG. 8 is a schematic drawing of the volume measurement system used in accordance with the invention.

The reference substrate is first tested as designated at 110 in the flow chart presented in FIG. 7 by inducing eddy currents in the reference substrate. Preferably, the means for inducing eddy currents is an eddy current inspection probe 140 (FIG. 8), such as a DT20P Probe manufactured by Zetec Inc., (Issaquah, Wash.) which is also used to measure the eddy current responses produced as described in more detail below. The eddy current inspection probe 140 consists of a reference coil and a test coil. An alternating electric current, such as a 200 kHz alternating current, is passed through the coils to produce a primary electromagnetic field. The test coil is situated in proximity to the substrate such that the primary electromagnetic field generated by the test coil penetrates the substrate and induces eddy currents within the substrate. The magnitude of the eddy currents produced is directly proportional to the amount of metal that is present within the primary electromagnetic field and thus inversely proportional to the volume loss within this field. In other words, the larger the amount of metal in proximity to the primary field, the larger the eddy currents and thus the magnitude of the eddy current response. The eddy currents generate a second electromagnetic field, which encompasses the test coil and has either a negating or complementary effect on the alternating electric current flowing through the test coil. The eddy current response can be described as a "fill factor" or "lift off", which can be described as a percentage of the primary field that penetrates the metal sample such that a fill factor of 100% equates to no volume loss at the measured location. The resulting current flowing through the test coil can then be compared to the current in the reference coil to determine the eddy current response. As will be apparent to those skilled in the art, the current flowing through the reference coil is unaffected by the eddy currents such that the difference in the current flowing through the reference coil and the test coil provides a measure of the magnitude of the eddy currents and, in turn, a measure of the amount of metal that is present within the primary electromagnetic field.

The actual eddy current responses for a plurality of locations within each sector on the surface of the reference substrate are measured using a measurement device such as the eddy current inspection probe described above. Preferably, the eddy current inspection probe is designed to have a measurement surface corresponding to the surface of the reference substrate. For example, a probe having a circular measurement surface can be used to measure the eddy current responses produced in a fastener hole. The eddy current inspection probe 140 can measure the actual eddy current response, but preferably measures the difference between the eddy current magnitude of a reference coil equating to a fill factor of 100% and the eddy current magnitude of a test coil relating to the actual eddy current magnitude at a certain location, as described above.

The eddy current response is typically measured at a plurality of locations at regular intervals along the x-axis and y-axis of the surface such that each sector on the surface of the reference substrate contains the same number of measurements. The measurements of the eddy current magnitudes in the sectors containing no flaws or defects (i.e., no volume loss) are averaged for each of the locations to provide a threshold or background noise level (T) designated at 114. This value becomes the offset value to normalize the remaining data to a zero baseline. The threshold level (T) is then subtracted from each of the measurements in the sectors containing defects or flaws to normalize the eddy current magnitudes for the locations within these sectors as shown at 116. The normalized eddy current magnitudes are then summed for each of the locations within each sector to produce a normalized eddy current for the sector as shown at 118.

Figure 10:
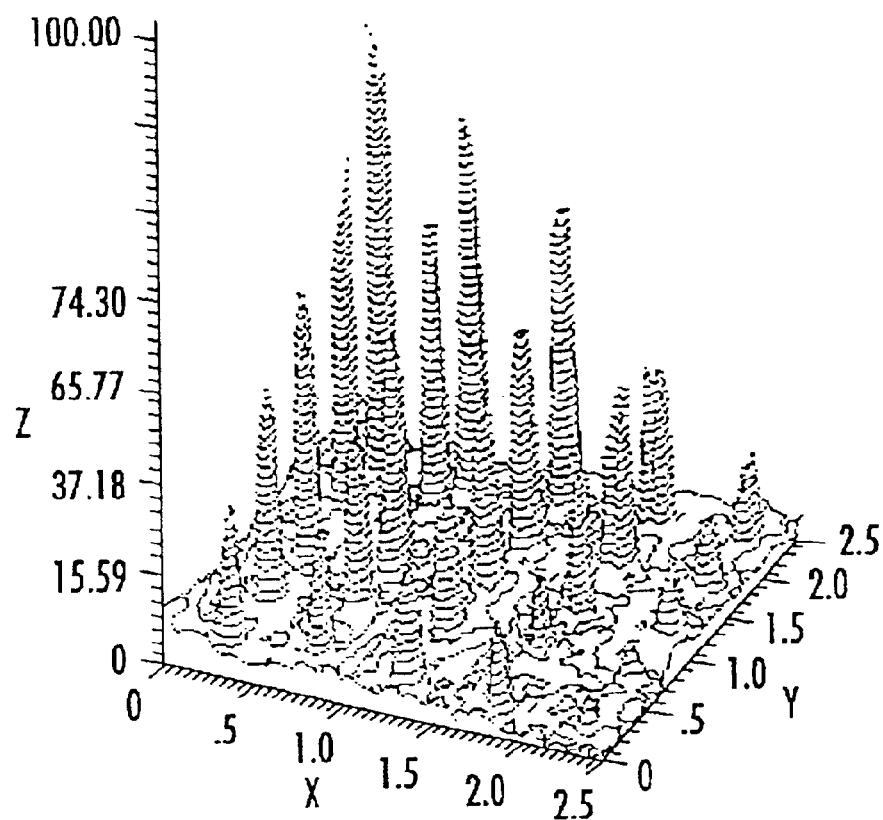
FIG. 10 illustrates the actual eddy current response obtained from the volumes of defects shown in FIG. 9 from the reference standard.

For purposes of illustration, FIG. 10 illustrates a 2.5 inches×2.5 inches scan area obtained by the scanning of a reference standard surface having positive volume losses as shown in FIG. 9. In order to produce the contour scan or C-Scan illustrated in FIG. 10 of the reference substrate of FIG. 3, a controller 142 (FIG. 8) controls the measurement device which scans the reference surface in the X direction and samples eddy current values at locations 144 every 0.050 inch. When the end of the sample area was reached, the measurement device is moved 0.050 inch in the Y direction and again moves across the surface in the X direction. This scanning process is repeated until the magnitudes of the eddy current responses across the entire scan area have been measured. Although the test area was scanned in this manner, other scan methods such as helical or raster scans can be used as long as the entire test area is scanned. The eddy current magnitudes for each sector 146 (FIG. 8) were then measured by summing the normalized measurements for each location in the sector 118 (FIG. 7 flow chart) and the resulting eddy current response for each sector was graphed in FIG. 10. The Z direction of FIG. 10 relates to percent of total scale wherein 100% relates to the sector having greatest volume loss.

The values in FIG. 10 can then be used to relate the predetermined volumes and predetermined surface areas for the sectors to the normalized magnitudes of the eddy current for the sectors. A preferred method of providing this relationship is to use the measurements for the sector having the greatest volume loss. The predetermined volume for the sector of greatest volume loss is divided by the normalized eddy current response for the sector and the surface area of the sector to produce a calibration factor $(C_f)$ representing the volume per unit area eddy response 120. The calibration factor $(C_f)$ can then be used for testing other surfaces. Although this is the preferred method of calibration, one or more of the sectors can be used as described above to produce the calibration factor $(C_f)$.

Once the system is calibrated, eddy currents are induced in a test surface in the same manner described in the calibration as designated at 122. The magnitude of the eddy current response produced in the test substrate is then measured along the test surface at a plurality of locations at regular intervals using a measurement device having a measurement area corresponding to the test surface as designated at 124. In order to provide accurate volumetric measurements, the intervals at which the eddy current magnitudes are measured are the same as those used in the calibration sequence. A threshold value $(T_{test})$ is then determined for the test substrate as designated at 126 by averaging the eddy current responses for the locations of no volume loss. The eddy current magnitudes at each location are then normalized by subtraction, the threshold value $T_{(test)}$ as designated at 128. The test surface is divided into sectors of predetermined surface area and the normalized eddy current magnitudes for the locations within each sector are summed to provide the normalized eddy current response for the sector as designated at 130. The normalized eddy current response and the surface area are then multiplied by the calibration factor $(C_f)$ 120 to produce the actual volume loss within the sector in cubic inches as designated at 132. The volume loss measurements on the test surface are determined using suitable converting means (such as a microprocessor) and can then be graphed to produce a contour map or C-scan of the test surface. The C-scan provides a true quantitative measurement of the volume loss due to corrosion or damage on the test surface and allows actual volume of the metal loss for each sector expressed in cubic inches.

Correlation between the fill factor and the amount of metal loss due to the corrosion damage in the sample permits the direct measurement and quantification of the amount of metal loss due to the corrosion activity. By properly calibrating the eddy current response to known volumes from reference standards, the metal loss resulting from corrosion damage detected can be quantified accurately. Once metal loss is detected and the amount of the loss is accurately quantified, a determination of a course of action for the test part such as replacement or repair of the part, if necessary, can be determined.

The present invention provides a method for the direct measurement and quantification of the three dimensional material volume loss along the surface and sub-surface profile of a substrate and thus more accurately depicts the profile of a substrate than obtained through conventional processes, which can only provide comparative measurements of a surface profile. See FIG. 4. The method of the invention thus allows a contour map of the surface of substrate to be determined illustrating the material lost due to corrosion, damage or other anomalies. See FIGS. 6 and 10.

Review of the data obtained from the inspection of the test specimens' faying surfaces indicated that resulting levels of corrosion damage measured for the components' faying surfaces were significantly less than the flaws associated with the reference standard plate. See Table 1. The levels of corrosion damage are presented in Table 1 by a corrosion index value, also graphically shown as the vertical axis in FIG. 6. It should also be restated that in reviewing these comparisons, the measured corrosion volumes of the test specimens were extremely small in magnitude compared to the reference standard plates. This supported the assessment made during a separate visual and macroscopic examination that there was minimal evidence of corrosion activity, of the test plates. The eddy current quantification technique of the present invention was actually sensitive enough to be registering discontinuities and imperfections in the metallic substrate itself, which were on the order of, or less than the reference standard flaw sizes. The tests compared varying corrosion protection methods. The wet sealant method is understood to refer to the application of a wet sealant to a component's faying surface at or after the time of component assembly. By contrast, the pre-coated sealant is understood to refer to the method by which components are coated prior to their assembly.

TABLE 1

Volumetric Corrosion Measurement of Component Faying Surfaces

| Test Specimen Assembly ID | Corrosion Protection | Corrosion 'Index' Value, X10$^{-6}$ in$^3$ |
|---|---|---|
| A1A | Wet-Sealant | 4.14 |
| A3A | Pre-Coated | 3.61 |
| A11A | Wet-Sealant | 3.56 |
| A12A | Pre-Coated | 4.04 |
| .006" × .018" × 0.250" Ref 'Flaw' | N/A | 28.5 |
| .006" × .018" × 0.188" Ref 'Flaw' | N/A | 20.9 |
| .006" Ø × 0.188" Ref 'Flaw' | N/A | 0.28 |

More advantageously, the method of the invention allows for the early determination of metal loss due to corrosion and damage, thereby allowing a determination as to the potential replacement or repair of the test substrate prior to failure of the substrate. The method of the invention can be used with various types of materials and can be used to measure volume losses even on indentations and projections such as around rivets and other fasteners. In addition, historical data can be collected for specific test articles along with the generation of other reports. The collection of historical data, permits the establishment of test schedules for various types of information, such as future test schedules, statistical error data regarding failed articles, which may be associated with specific regions in the X-Y plane of the test article such as aircraft wings and control surfaces.

Many modifications and other embodiments of the invention will come to the mind of one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A non-invasive process for detecting a volume loss within a test substrate comprising the steps of:
   inducing higher frequency and lower frequency eddy current fields in the test substrate;
   measuring the magnitude of the eddy currents produced within the test substrate at the surface of the test substrate;
   determining a difference between the higher frequency eddy current field and the lower frequency eddy current field; and
   determining the volume loss within the test substrate based, at least in part, upon the difference between the higher frequency eddy current field and the lower frequency eddy current field.

2. The method according to claim 1, wherein the substrate surface is measured at a plurality of surface locations.

3. The method according to claim 2 wherein the eddy current magnitude is the sum of the eddy current magnitudes at the plurality of surface locations.

4. The method according to claim 1, wherein the eddy current fields are induced substantially simultaneously.

5. The method according to claim 1, wherein the subsurface comprises a surface opposite of the test substrate at which the magnitude of the eddy currents is measured.

6. The method according to claim 1, wherein the subsurface material flaw is located more than about 0.100 inch from the material surface.

7. The method according to claim 1, wherein the subsurface material flaw is located a distance from the surface of from about 0.100 inch to about 0.750 inch.

8. The method according to claim 1 further comprising the steps of:
   inducing eddy currents in a reference substrate;
   measuring the magnitude of the eddy current produced within the reference substrate at a plurality of locations of known volume loss on the surface of the reference substrate; and
   determining a calibration factor ($C_f$) based on the measured magnitudes at the locations on the reference substrate.

9. The method according to claim 8 wherein the step of:
   determining the calibration factor ($C_f$) comprises selecting a sector of predetermined volume loss and surface area, summing the eddy current measurements for the locations within the sector, to provide an eddy current magnitude for the sector and dividing the predetermined volume loss of the sector by the eddy current magnitude for the sector and the surface area of the sector to produce calibration factor ($C_f$).

10. The method according to claim 1 further comprising the steps of:
   inducing eddy currents in a reference substrate having a surface comprising a plurality of sectors of predetermined surface area and predetermined volume loss such that at least a portion of the sectors have minimum volume loss and at least a portion of the sectors have a positive volume loss;
   measuring the magnitude of the eddy current produced within the reference substrate at a plurality of locations within each sector;
   averaging the eddy current magnitudes measured for the locations having minimal volume loss to provide a threshold level (T);
   normalizing the eddy current magnitudes for the locations in the sectors having positive volume loss by subtracting the threshold level (T) from the measured magnitudes at the locations;
   summing the normalized eddy current magnitudes measured at each of the locations in a sector to provide a normalized eddy current magnitude for the sector; and
   determining a calibration factor ($C_f$) representing the measured volume per unit area eddy current magnitude by dividing the predetermined volume loss of the sector by the normalized eddy current magnitude for the sector and the surface area of the sector.

11. The method according to claim 10, wherein at least a portion of the sectors have no volume loss.

12. The method according to claim 10, wherein the eddy currents are induced substantially simultaneously.

13. The method according to claim 10, wherein the sub-surface comprises an opposing surface.

14. A method for measuring the sub-surface volume loss of a metal substrate comprising the steps of:

inducing high and low frequency eddy current fields substantially simultaneously to a metal reference substrate sub-surface having a sub-surface comprising a plurality of sectors of predetermined surface area and predetermined volume loss such that at least a portion of the sectors have minimum volume loss and at least a portion of the sectors have a positive volume loss;

measuring the magnitude of the eddy current fields produced within the reference substrate at a plurality of locations within each sector;

averaging the eddy current field magnitudes measured for the locations in the sectors having minimum volume loss to provide a threshold level (T);

subtracting the threshold level (T) from the measured magnitudes for the locations in the sectors having positive volume loss to provide a normalized eddy current field magnitude for each location;

summing the normalized eddy current magnitudes measured at each of the locations in the sector having the greatest volume loss to provide a normalized eddy current field magnitude for the sector of greatest volume loss;

dividing the predetermined volume of the sector of greatest volume loss by the normalized eddy current magnitude for the sector of greatest volume loss and the surface area of the sector of greatest volume loss to produce a calibration factor ($C_f$) representing the measured volume per unit area eddy current magnitude;

inducing high and low frequency eddy current fields in a metal test substrate;

subtracting the high frequency eddy current field from the low frequency eddy current field to achieve a resulting eddy current field;

measuring the magnitude of the resulting eddy current field produced within the test substrate at a plurality of sub-surface locations within sectors of predetermined surface area;

subtracting the resulting measured eddy current field at the locations from the threshold value (T) to produce normalized eddy current magnitudes at the locations;

summing the normalized eddy current magnitudes for the locations within each sector to produce a normalized eddy current magnitude for each sector; and multiplying the normalized eddy current magnitudes for each sector by the calibration factor ($C_f$) and by the surface area of the sector to provide volumetric measurements of the volume loss at the locations thereby providing a surface profile of volume loss on the test surface.

15. The method according to claim 14, wherein a portion of the sectors have no volume loss.

16. The method according to claim 14, wherein the high and low frequency eddy current fields are induced from a first surface, and wherein the sub-surface comprises a surface opposite the first surface.

17. A system for producing a profile of the volume loss along a surface of a test substrate comprising:

a plurality of eddy current inducers positioned at a first surface for simultaneously inducing eddy current fields having varied frequencies beneath the surface of the test substrate;

a measurement device for measuring the magnitude of the eddy current fields produced beneath the substrate surface; and a converter device for converting the measured magnitudes at the locations to corresponding volume losses on a second surface.

18. The system according to claim 17 wherein said measurement device is an eddy current inspection probe having an inspection surface which corresponds to the test surface.

19. The system according to claim 17 wherein the plurality of eddy current inducers generate a primary magnetic field in the test substrate.

20. The system according to claim 17 wherein the test surface comprises sectors of predetermined surface area and the conversion device comprises:

an eddy current normalizer to normalize magnitudes measured on the surface of the test substrate;

means for summing the normalized eddy current magnitudes within a sector to provide a normalized eddy current magnitude for the sector; and means for multiplying the normalized eddy current magnitude of the sector by the surface area of the sector and a calibration factor ($C_f$) representing the volume per unit area eddy current magnitude to calculate the actual volume loss on the surface of the test substrate within each sector.

21. The system according to claim 17, wherein the second surface is an opposite the first surface.

22. The system according to claim 17, wherein the plurality of eddy current fields are induced substantially simultaneously.

* * * * *